United States Patent [19]

Clerici et al.

[11] Patent Number: 5,037,790
[45] Date of Patent: Aug. 6, 1991

[54] SOLID CATALYST FUNCTIONALIZED WITH SULFONIC GROUPS, PROCESS FOR PERPARING IT AND ITS USE

[75] Inventors: Mario G. Clerici, Milan; Giulio Alberti, Perugia; Marinella Malentacchi, Arezzo; Giuseppe Bellussi, Piacenza; Aldo Prevedello; Carlo Corno, both of Milan, all of Italy

[73] Assignee: Eniricerche S.p.A., Milan, Italy

[21] Appl. No.: 488,639

[22] Filed: Mar. 5, 1990

[30] Foreign Application Priority Data

Mar. 10, 1989 [IT] Italy ................... 19736 A/89

[51] Int. Cl.$^5$ ............................................. C08F 4/64
[52] U.S. Cl. .................................. 502/162; 502/168; 502/208; 502/214
[58] Field of Search ............... 502/162, 168, 208, 214

[56] References Cited

U.S. PATENT DOCUMENTS 4,394,255 7/1983 Kukes et al. ..................... 502/208
4,524,143 6/1985 Vanderpool ..................... 502/208
4,855,399 8/1989 Van Doorn et al. ............... 502/168

Primary Examiner—Patrick P. Garvin
Assistant Examiner—Brent M. Peebles
Attorney, Agent, or Firm—Hedman, Gibson, Costigan and Hoare

[57] ABSTRACT

Disclosed is a solid catalyst functionalized with sulfonic groups, containing from 20 to 99% by weight of silica, with the residual percentage being definable by means of the formula:

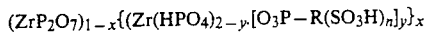

$$(ZrP_2O_7)_{1-x}\{(Zr(HPO_4)_{2-y}[O_3P-R(SO_3H)_n]_y\}_x$$

wherein:
R is an either linear or branched linear hydrocarbon radical containing from 1 to 10 carbon atoms, or an aryl radical;
x is a numeral higher than 0 and of up to 1;
y is a numeral higher than 0 and of up to 2;
n is either 1 or 2;
with said catalyst furthermore showing silicon-oxygen-phosphorus bonds on N.M.R. examination and being amorphous or substantially amorphous when examined under X rays.

The catalyst is useful in the acidic catalysis, for example in reactions of hydrocarbon conversion, such as alkylation, isomerization and oligomerization. The product according to the present invention is furthermore useful as an ion exchange agent.

16 Claims, 1 Drawing Sheet

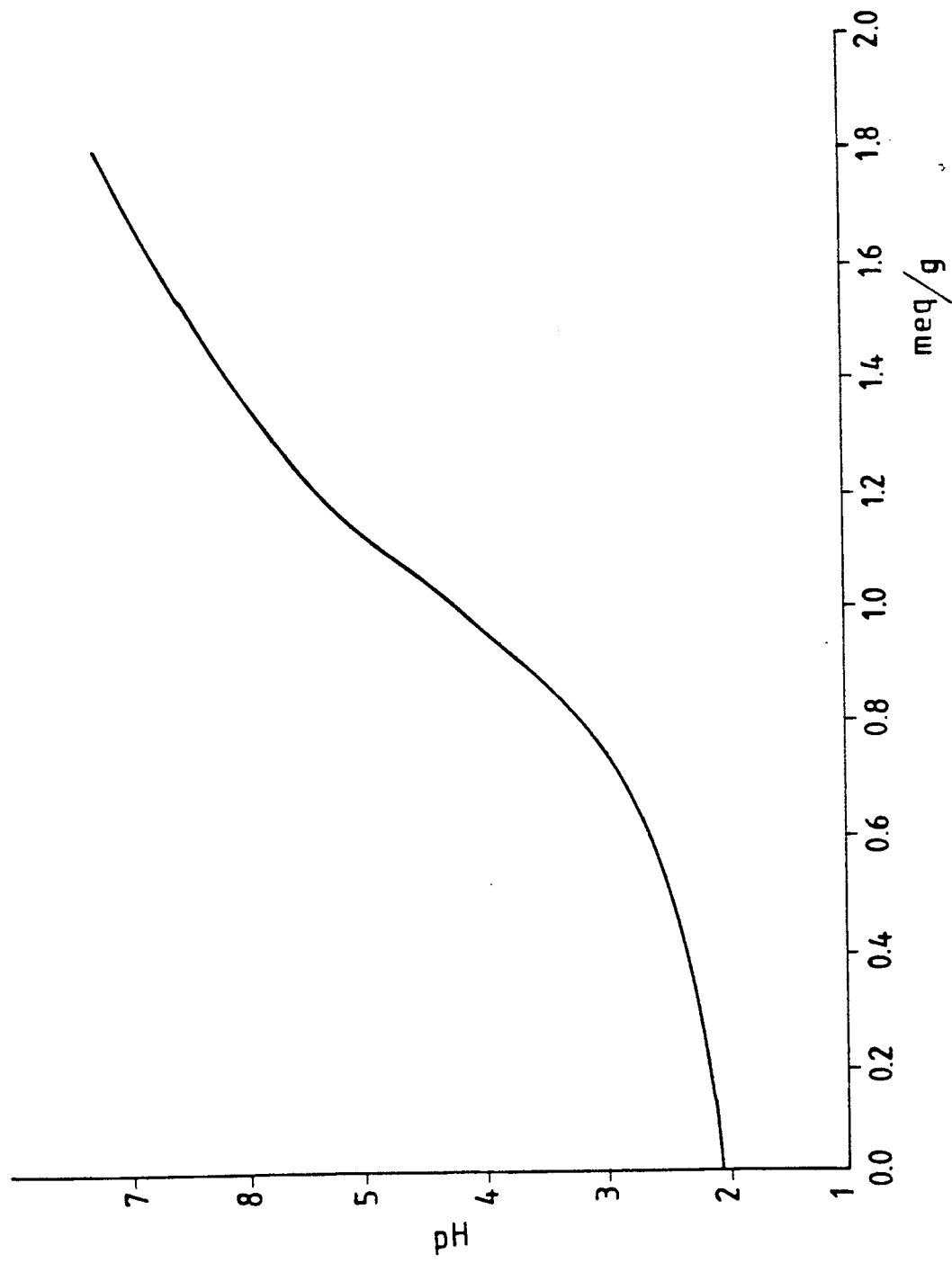

SOLID CATALYST FUNCTIONALIZED WITH SULFONIC GROUPS, PROCESS FOR PERPARING IT AND ITS USE

The present invention relates to a solid catalyst functionalized with sulfonic groups, to the process for preparing it and to its use in the acidic catalysis, and as an ion exchange agent.

Various acidic catalysts are known in the art and are used in the acidic catalysis, for example in the processes of hydrocarbon conversion, such as isomerization, oligomerization and alkylation.

In European patent application publication No. 10,857 inorganic, polymeric solids based on zirconium phosphate and bearing an organic group, including . a sulfonated organic group, are generally disclosed. These polymeric solids are useful as catalysts, adsorbents, ion exchange agents and complexing agents.

In U.S. Pat. Application No. 280,556 filed on Dec. 6, 1988, in the same Applicant's name, a special material is disclosed, which is essentially constituted by a dispersion of alpha zirconium phosphate in silica. Such a material displays activities as an acidic catalyst and as an ion exchange agent.

The present Applicant has found now that the $$O_3P-OH$$

groups of the zirconium hydrogen phosphate contained in the catalyst disclosed by the hereinabove cited Italian patent application can be either partially or totally replaced by $$O_3P-R-SO_3H$$

groups (wherein R=an organic radical). Such a replacement makes it possible new and useful materials to be obtained, which are active in the acidic catalysis, as well as ion exchange agents.

The present Applicant could also find that this catalytic activity is surprisingly high, as compared to the activity performed by the catalysts known from the prior art, functionalized with sulfonic groups.

In accordance therewith, according to a first aspect thereof, the present invention relates to a solid catalyst functionalized with sulfonic groups, which contains from 20 to 99% by weight of silica, with the residual percentage being definable by means of the formula:

$$(ZrP_2O_7)_{1-x}\{Zr(HPO_4)_{2-y}\cdot[O_3P-R(SO_3H)_n]_y\}_x$$

wherein:

R is either a linear or branched, aliphatic hydrocarbon radical containing from 1 to 10 carbon atoms, or an aryl radical;

x is a numeral higher than 0 and of up to 1;

y is a numeral higher than 0 and of up to 2;

n is either 1 or 2; with said catalyst furthermore showing silicon-oxygenphosphorus bonds on N.M.R. examination and being amorphous or substantially amorphous when examined under X rays.

In the preferred form of practical embodiment, the catalyst according to the present invention contains an amount of from 50 to 80% by weight of silica, and in the hereinabove reported formula:

R is an aliphatic hydrocarbon radical containing from 2 to 6 carbon atoms, or a benzene radical;

x is a numeral comprised within the range of from 0.05 to 0.7, and

X is a numeral comprised within the range of from 0.5 to 1.8.

The catalyst according to the present invention can be prepared by means of a process which comprises the following steps:

(1) lamellar crystalline zirconium phosphate is delaminated by means of the intercalation of an amine, by operating in a preferably aqueous medium, in order to obtain a colloidal dispersion of delaminated zirconium phosphate;

(2) the dispersion prepared in the step (1) is mixed with colloidal silica;

(3) the resulting mixture is gelled by heating, with an acidic gelling agent being possibly added;

(4) the gel prepared in the step (3) is dried and calcined;

(5) the calcined solid is reacted with a phosphonoalkylsulfonic acid or a phosphono-aryl-sulfonic acid.

In the step (1) of the process according to the present invention crystalline, lamellar alpha zirconium phosphate $$(\alpha-Zr(HPO_4)_2\cdot H_2O)$$

is preferably used. Said zirconium phosphate is suspended in water and to the resulting suspension an amine, such as an alkylamine or an alkanolamine, and preferably an n-alkyl amine, such as n-propyl amine, is added. The addition of the amine is advantageously carried out at a slow addition rate, with the reaction mass being kept vigorously stirred, by operating under room temperature conditions. After the end of the addition of the amine, stirring is continued until a colloidal dispersion of delaminated alpha zirconium phosphate is obtained. For further details on the treatment of delamination, reference is made to the specification of hereinabove cited U.S. Pat. Application No. 280,556.

In the step (2) of the process, the dispersion obtained in the step (1) is mixed with colloidal silica. For that purpose, that grade of colloidal silica can be used, which is known under the trade mark "LUDOX" (a product by Du Pont). As an alternative, such a colloidal silica can be prepared by means of the controlled hydrolysis of a tetra-alkyl silicate in the presence of an organic base, such as, e.g., tetrapropylammonium hydroxide.

The resulting mixture is gelled in the step (3) by heating at a temperature of 70°–90° C. In order to speed up the gelification, an acid, and preferably acetic acid, can be added to the mixture.

The resulting gel is dried and calcined in the step (4) of the process. The operation of calcination is carried out in air at a temperature comprised within the range of from 500° to 700 ° C., and preferably of the order of 600°–650° C. The operation of calcination is used in order to burn the organic portion and to regenerate zirconium phosphate in the acidic form. In such a process a partial transformation of Zr(HPO$_4$)$_2$ into ZrP$_2$O$_7$ also occurs, and Si—O—P bonds are formed as well. The resulting solid is hence a dispersion of $$(ZrP_2O_7)_{1-x}[Zr(HPO_4)_2]_x$$

in silica. Such a solid has a high surface area, typically of the order of 400–500 m$^2$/g.

In the step (5) of the process, the calcined solid is dispersed in an inert diluent, and preferably in water, and to the so obtained dispersion a phosphonoalkylsulfonic acid or a phosphonoarylsulfonic acid is added in order to accomplish an exchange reaction with the phosphoric acid of zirconium phosphate, and obtain the catalyst of the present invention. Typical examples of phosphonoalkylsulfonic acids or of phosphonoarylsulfonic acids are 2-phosphono-ethane-sulfonic acid, meta-phosphonobenzenesulfonic acid and phosphonobenzene-3,5-disulfonic acid. In the exchange reaction, a concentration of the phosphono-alkyl-sulfonic acid or phosphono-aryl-sulfonic acid is used, which is comprised within the range of from 0.1 molar up to the saturation value, and the reaction is carried out at a temperature comprised within the range of from room temperature (20°–25° C.) up to about 100° C. The solid product resulting from the reaction is separated, is washed with water or with a suitable organic solvent (e.g., acetone and diethyl ether), and is dried at temperatures not higher than about 250° C. The so obtained catalyst according to the present invention is a solid product having the chemical composition as hereinabove reported, and at N.M.R. analysis it shows a resonance signal which is typical of silicon-oxygen-phosphorus bonds, that demonstrates the existence of a chemical linkage between silica and the residual portion of the catalyst. Furthermore, the catalyst is amorphous, or substantially amorphous when examined under X rays.

According to a particular form of practical embodiment of the process according to the present invention, the gel obtained in the step (3) is submitted to regeneration in order to yield back the hydrogen form of the zirconium phosphate before the treatments of drying and calcination. This regeneration is advantageously carried out by dilution with an acid, and preferably with acetic acid.

In any case the resulting gel can be submitted, if so desired, to a treatment of shaping by means of an extrusion process, or the like, in order to convert the solid into a desired physical form for said solid to be suitable for its end use as a catalyst.

According to a further form of practical embodiment of the process according to the present invention, the mixture obtained in the step (2) is submitted to spray-drying and the so obtained dried solid is directly sent to the step (5) in order to undergo the calcination.

The so obtained catalysts according to the present invention show a heat stability, depending on the type of phosphonic acid used, which may arrive up to temperatures of 200°–300° C. Said catalysts are active as acidic catalysts, in the chemical reactions which require an acidic catalysis, such as, e.g., in the reactions of conversion of the hydrocarbons, such as the reactions of isomerization and oligomerization of olefins, and of alkylation of the aromatic hydrocarbons with olefins. Examples of such reactions are: isomerization of butene-1 into butene-2, oligomerization of octene-1; alkylation of toluene with propylene and alkylation of benzene with propylene and with octene-1. Another sector of application is the sector of ion exchange agents.

BRIEF DESCRIPTION OF THE DRAWING

The drawing shows the titration curve obtained in Example 14.

The following experimental examples are reported in order to better illustrate the instant invention.

EXAMPLE 1

A) Preparation of delaminated alpha zirconium phosphate 6.6 g of crystalline alpha zirconium phosphate [$\alpha$-$Zr(HPO_4)_2.H_2O$] with lamellar structure, having an average crystal dimension of about 15 $\mu$m and a surface area of 0.2 $m^2$/g, is suspended in 680 ml of water and to the resulting suspension 110 ml of an 0.2 M aqueous solution of n-propylamine is added. The addition is gradually carried out over a time of about 4 hours, with vigorous stirring. The mixture is left standing for the successive 20 hours and a colloidal dispersion of delaminated alpha zirconium phosphate is obtained.

B) Preparation of the solution of silica

To 36.7 g of an aqueous solution of tetrapropylammonium hydroxide at 19% by weight, pre-heated at about 40° C., 39.7 g of tetraethyl silicate is added with stirring and the resulting mixture is kept stirred until a clear solution is obtained. The solution is cooled down to room temperature and the evaporation losses are replenished with demineralized water.

C) Preparation of the dispersion of delaminated $\alpha$-$Zr(HPO_4)_2.H_2O$, in silica The suspension of zirconium phosphate obtained in the (A) step is put with strong stirring and to it the solution of silica obtained in the (B) step is added. When the whole mixture is homogenized, 36 ml of 1 M acetic acid is added with stirring and the resulting mixture is heated at 80° C. until the gelation of the system and the drying of the resulting gel are achieved. In the operations of addition and mixing, 50–100 ml of water can be used in order to wash the vessels. The material is then gradually heated to 650° C. and is then calcined in air at this temperature for about 3 hours, until the complete combustion of the organic portion is achieved. A white solid is thus obtained, which contains about 64% of $SiO_2$, with the residual percentage to 100 being constituted by zirconium phosphate-pyrophosphate. In order to obtain solids with different percentages of silica, the procedure is the same as disclosed, with different proportions of (A) and (B) solutions being mixed with each other.

D) Preparation of phosphono-benzene-sulfonic acid 101 g (0.64 mol) of benzenesulfonic acid (Fluka) and 400 ml (6.03 mol) of chlorosulfonic acid (Fluka) are charged to a flask of 2,000 ml of capacity equipped with mechanical blade stirrer, thermometer, bubble condenser (and subsequent sodium hydroxide-water trap for fixing hydrogen chloride and any chlorosulfonic acid possibly contained in the escaping vapours) and nitrogen inlet way. The reaction mixture is heated up to 100°. The temperature is maintained for 1 hour at that value, and the reaction mixture is then heated up to 120° C. for a further 2 hours. At the end, the solution is cooled down to 5°–10° C. and is charged to a separator funnel.

In the meantime, about 400 g of ground ice is charged to a glass of 2 liters of capacity. The reaction mixture is poured very slowly from the separator funnel into the ice, with the temperature being kept lower than 0° C. The phosphono-benzene-sulfonyl chloride which precipitates is rapidly filtered off and is washed with a very small amount of ice water (about 40 ml). It is then dissolved in about 60-70 ml of water and is concentrated up to nearly dryness under vacuum at room temperature (within a time of about 4 hours) in order to hydrolyse the sulfonyl chloride into the acid, and simultaneously remove the hydrogen chloride resulting from the reaction. The resulting concentrated solution is then diluted with water and neutralized with an aqueous solution of sodium hydroxide. The resulting solution, of deep gray colour, is treated with animal charcoal, is centrifuged and is finally concentrated to dryness, first under the vacuum of the water pump and then inside a vacuum oven at 50°-60° C. for about 10 hours. A solid product (117 g) is obtained which contains (ionic chromatography) 6.5% of chlorine and 3.5% of sulfate. The amount of the residual water is Of 0.54% (according to Karl Fischer in pyridine).

E) Preparation of the solid catalyst functionalized with sulfonic groups 238 g of 1M meta-phosphonobenzene-sulfonic acid in aqueous solution is mixed with 70 g of the dispersion of alpha zirconium phosphate in silica obtained in the (B) step. The mixing is carried out inside a closed vessel. The temperature is increased up to 80° C. and is kept at this value for 20 days. The reaction mixture is then cooled, the separated solid is filtered off, the recovered solid is washed with acetone and water and is dried at 90° C. The solid catalyst of benzenesulfonic acid is thus obtained which, at the chemical analysis, shows a silica content of 63.5% by weight, with the balance to 100 having the following composition:

$(ZrP_2O_7)_{0.05}[Zr(HPO_4)_{1.16}(O_3P-C_6H_4SO_3H)_{0.84}]_{0.95}$

The catalyst, submitted to 29Si-MAS-NMR analysis, displays a main signal at $-111$ ppm, to be attributed to a silicon atom bonded through respective oxygen bridges to four other silicon atoms, and a shoulder at $-102$ ppm, which corresponds to the frequency of resonance of a silicon atom bonded by oxygen bridges to three silicon atoms and to a phosphorus atom. When examined under X rays, the catalyst does not show the typical bands of crystalline zirconium phosphate.

EXAMPLE 2

The process is carried out in the same way as of the (E) step of Example 1, by bringing 85 g of metaphosphonobenzene-sulfonic acid in 0.5 M solution into contact with 50 g of the dispersion of alpha zirconium phosphate in silica, obtained as disclosed in the (C) step of Example 1, and with the suspension being kept standing to 80° C. for 20 days.

A solid catalyst of benzenesulfonic acid is obtained which, at the chemical analysis, shows a silica content of 55% by weight, with the balance to 100 having the following composition:

$(ZrP_2O_7)_{0.15}[Zr(HPO_4)_{1.25}(O_3P-C_6H_4SO_3H)_{0.75}]_{0.85}$

The 29Si-MAS-NMR analysis and the X-ray analysis of the catalyst yield similar results to those as obtained with the catalyst of Example 1.

EXAMPLE 3

The process is carried out in the same way as of the (E) step of Example 1, by bringing 12.2 g of phosphobenzene-3,5-disulfonic acid in 0.5 M solution into contact with 54 g of the dispersion of alpha zirconium phosphate in silica, obtained as disclosed in the (C) step of Example 1, and with the suspension being kept standing to 80° C. for 20 days.

A solid catalyst of benzenesulfonic acid is obtained which contains 57% by weight, with the balance to 100 having the following composition:

$(ZrP_2O_7)_{0.05}\{Zr(HPO_4)_{1.8}\cdot[O_3P-C_6H_3(SO_3H)_2]_{0.2}\}_{0.95}$

The 29Si-MAS-NMR analysis and the X-ray analysis of the catalyst yield similar results to those as obtained with the catalyst of Example 1.

EXAMPLE 4

The process is carried out in the same way as of the (E) step of Example 1, by bringing 6.45 g of 2-phosphonoethane-sulfonic acid in 0.5 M solution into contact with 4.42 g of alpha zirconium phosphate dispersed in silica, prepared as disclosed in the (C) step of Example 1, and with the suspension being then kept standing at 80° C. for 20 days.

A solid catalyst of ethanesulfonic acid is obtained, which shows a silica content of 64% by weight, with the balance to 100 having the following composition:

$(ZrP_2O_7)_{0.05}[Zr(HPO_4)_{1.43}(O_3P-C_2H_4SO_3H)_{0.57}]_{0.95}$

The 29Si-MAS-NMR analysis and the X-ray analysis of the catalyst yield similar results to those as obtained with the catalyst of Example 1.

EXAMPLE 5

Isomerization of butene-1

10 ml of anhydrous heptane, 1 g of butene-1 and 300 mg of the catalyst prepared in Example 1 are charged to a two-neched flask.

The flask is closed with a pierceable stopper of silicone rubber, so as to make it possible samples for analysis to be periodically drawn. The flask is kept at the constant temperature of 60° C. with stirring. The reaction products are analyzed by gas-chromatography on a column of 1.8 meters of length, packed with Poropack PS, at the temperature of 160° C. The results obtained are reported in the following table.

TABLE

| Time | 60 minutes | 150 minutes | 330 minutes |
| --- | --- | --- | --- |
| 1-butene (%) | 88.3 | 77.3 | 59.7 |
| cis-2-butene (%) | 5.3 | 10.7 | 19.2 |
| trans-2-butene (%) | 6.4 | 12.0 | 21.1 |

EXAMPLE 6

Oligomerization of octene-1

8 ml of octene-1 and 0.8 g of the catalyst prepared in Example 1 are charged to a small glass autoclave and the resulting mixture is heated to 130° C. 3.5 hours later the reaction mixture is analysed by gas-chromatography using a column of 1.2 m of length packed with SP 2100 at 3%, under temperature programmed conditions from 100° C.(5 minutes) up to 300° C. (temperature increase rate 30° C./minute). The reaction mixture is constituted by isomerized octene 41%, dimers 47%, trimers 8.8% and tetramers 2.1%.

The catalyst recovered by centrifugation at the end of the first test is washed with octene-1 and is used again in octene-1 oligomerization, which is carried out by operating under the hereinabove reported conditions. The products obtained after 3.5 hours of reaction show the following composition: octene 78%, dimers 20% and trimers 2%.

The catalyst recovered by centrifugation at the end of the second test is hot-washed twice with 5 ml of petroleum ether (under refluxing conditions for 30 minutes), twice with 5 ml of benzene (under refluxing conditions for 30 minutes) and then with 5 ml of methanol (under refluxing conditions for 30 minutes). The filtered off catalyst is dried under vacuum for 10 hours at 100° C. and is used once more in the oligomerization of octene-1, which is carried out by operating under the above reported conditions. The products obtained after 3.5 hours of reaction display the following composition: octene 42.5%, dimers 45%, trimers 8.5% and tetramers 2%.

EXAMPLE 7

Alkylation of toluene with propylene 3 ml of toluene, 0.4 g of propylene and 400 mg of the catalyst prepared in Example 1 are charged to a small glass autoclave and the resulting mixture is heated to 110° C. for 4 hours. As the reaction proceeds, the pressure decreases. At the end the reaction products are analyzed by gas-chromatography on a column of 1.2 m of length packed with SP 2250 at 3%, under temperature programmed conditions from 60° C. (5 minutes) up to 150° C. (temperature increase rate 25° C./minute). The reaction products have the following composition: toluene 73%, isopropyl-toluene 22% and di-isopropyl-toluene 2%.

EXAMPLE 8

Alkylationa of benzene with octene-1

1.9 ml of octene-1, 2.1 ml of benzene and 0.41 g of the catalyst prepared in Example 2 are charged to a small glass autoclave. The resulting mixture is heated to 110° C. with stirring, and samples are drawn over time in order to check the reaction course. The samples are analyzed by gas-chromatography on a column of 1.2 m of length packed with SP 2250 at 3%, under temperature programmed conditions from 100° C. (5 minutes) up to 200° C. (temperature increase rate 25° C./minute). After 4 hours, the reaction mixture results to be composed by octylbenzenes 17%, dioctylbenzenes 0.8%, with the residual 82% being constituted by unreacted benzene and octene.

EXAMPLE 9

Synthesis of cumene 30 mL of benzene, 4.1 g of the catalyst prepared in the same way as of Example 1 and 4 g of propylene are charged to a small glass autoclave. The autoclave is heated to 150° C. while the suspension is kept vigorously stirred. At regular time intervals samples are drawn and are analysed by gas-chromatography on a column of 1.2 m of length packed with SP 2250 at 3%, under programmed temperature conditions from 60° C. (5 minutes) up to 150° C. (temperature increase rate 25° C./minute). After 4 hours, the composition of the reaction mixture is as follows: benzene 67%, cumene 24%, diisopropylbenzene 6.5%.

EXAMPLE 10

Oligomerization of octene-1

8 ml of octene-1 and 0.82 g of the catalyst prepared in Example 4 are charged to a small glass autoclave. The resulting mixture is heated to 130° C. At regular time intervals samples are drawn and are analysed by gas-chromatography on a column of 1.2 m of length packed with SP 2100 at 3%, under programmed temperature conditions from 100° C. (5 minutes) up to 300° C. (temperature increase rate 30° C./minute). After 4 hours, unreacted octene is 88% and its dimers are 11%.

EXAMPLE 11

Oligomerization of octene-1

The process of octene-1 oligomerization is carried out in the same way as of preceding Example 10, with the catalyst prepared in Example 3 being used. After 3 hours unreacted octene is 78% and its dimers and trimers respectively are 20% and 1%.

EXAMPLE 12

Alkylation of benzene with octene-1

4.2 ml of benzene, 3.8 ml of octene-1 and 0.8 g of the catalyst prepared in Example 4 are charged to a small glass autoclave. The resulting mixture is heated to 110° C., with stirring. At regular time intervals samples are drawn and are analysed by gas-chromatography on a column of 1.2 m of length packed with SP 2250 at 3%, under programmed temperature conditions from 100° C. (5 minutes) up to 200° C. (temperature increase rate 25° C./minute). After 4 hours, the reaction mixture contains benzene 64%, octene 31% and octylbenzene 5%.

EXAMPLE 13

Alkylation of benzene with octene-1

The process is carried out in the same way as of Example 12, with the catalyst of Example 3 being used. After 4.5 hours the reaction mixture contains benzene 52%, octene 12%, octylbenzene 32% and dioctylbenzene 3%.

EXAMPLE 14

1 g of compound prepared in the same way as of Example 1, having the following composition: 58.6% of $SiO_2$ and 41.4% of:

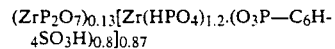

$(ZrP_2O_7)_{0.13}[Zr(HPO_4)_{1.2}.(O_3P-C_6H_4SO_3H)_{0.8}]_{0.87}$ is dispersed in 100 ml of a 0.1 M solution of NaCl. The solution is then titrated with 0.1 M NaOH, with an automatic titrator METTLER DK15 up to an end pH value of 7. The titration curve reported in the figure displayed in the hereto attached drawing table shows that the protons of the acidic groups $-SO_3H$ and $\equiv P-OH$ contained in the solid are easily exchanged by sodium ions. Inasmuch as the total ion exchange capacity computed on the basis of the composition of the solid is of 1.9 meq/g, the titration curve demonstrates that approximately 90% of the protons of the acidic groups $-SO_3H$ and $\equiv P-OH$ are substituted at pH=7.

EXAMPLE 15

0.51 g of catalyst prepared in the same way as of Example 1 and dried under vacuum at 80° C. for 8 hours, 3.05 g of $C_{14}$ olefins, 8.71 g of benzene and 0.316 g of n-dodecane (internal standard for gas-chromatography) are charged to a glass autoclave of about 30 ml of volume. The olefin fraction has the following composition, as determined by gas-chromatographic analysis: n-tetradecane 5.13% by weight, n-pentadecane 0.18% by weight, isomer n-tetradecenes (the isomerism is due to the position of the double bond) 87.4%, n-pentadecenes 3.68% by weight, aromatics and dienes 3.61%.

The suspension is heated with vigorous stirring for 3 hours at 150° C. (internal temperature), with the pressure simultaneously decreasing from 4.1 to 3.5 atm. After the reaction mixture being cooled and the catalyst being filtered off, the reaction mixture is analysed by gas-chromatography and mass-spectrometry, by using a column of 1.2 m of length packed with SP 2100 at 10%, under programmed temperature conditions from 170° C. (8 minutes) up to 200° C. (temperature increase rate 30° C./minute). It results that the olefins have reacted for more than 93% with tetradecylbenzenes and small amounts of pentadecylberzenes being formed as the reaction products.

EXAMPLE 16

0.51 g of catalyst prepared in the same way as of Example 1 and activated as disclosed in Example 15, 13.5 g of olefins having the same composition as described in above Example 15 and 0.317 g of n-dodecane (gaschromatographic internal standard) are charged to a glass flask having a volume of about 25 ml. The suspension is heated at 160° C. for 5 hours, with vigorous stirring, under an inert atmosphere of dry nitrogen. After the reaction mixture being cooled and the catalyst being filtered off, the reaction mixture is analysed by gaschromatography on a column of 80 cm of length packed with SP 2100 at 3%, under programmed temperature conditions from 180° C. (for 5 minutes) up to 300° C. (temperature increase rate 30° C./minute). The conversion of the olefins results to be of 48.6%; the resulting products are the dimers (yield 38%), the trimers (yield 7.7%) and the tetramers (not quantified).

We claim:

1. Solid catalyst functionalized with sulfonic groups, containing from 20 to 99% by weight of silica, with the residual percentage being definable by means of the formula:

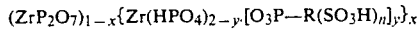

$(ZrP_2O_7)_{1-x}\{Zr(HPO_4)_{2-y}[O_3P-R(SO_3H)_n]_y\}_x$ wherein:
R is an either linear or branched aliphatic hydrocarbon radical containing from 1 to 10 carbon atoms, or an aryl radical;
x is a numeral higher than 0 and of up to 1;
y is a numeral higher than 0 and of up to 2;
n is either 1 or 2;
with said catalyst furthermore showing silicon-oxygen-phosphorus bonds on N.M.R. examination and being amorphous or substantially amorphous when examined under X rays.

2. A catalyst according to claim 1, having from 50 to 80% by weight of silica, and wherein in the formula:
R is an aliphatic hydrocarbon radical containing from 2 to 6 carbon atoms, or a benzene radical;
x is a numeral comprised within the range of from 0.05 to 0.7, and
y is a numeral comprised within the range of from 0.5 to 1.8.

3. A process for preparing the catalyst according to claim 1, comprising:
(1) delaminating lamellar crystalline zirconium phosphate by means of the intercalation of an amine in an aqueous medium to obtain a colloidal dispersion of delaminated zirconium phosphate;
(2) mixing the dispersion prepared in step (1) with colloidal silica;
(3) gelling the resulting mixture by heating;
(4) drying and calcining the gel prepared in step (3); and
(5) reacting the calcined solid with a phosphonoalkyl-sulfonic acid or a phosphono-aryl-sulfonic acid.

4. A process according to claim 3, wherein in step (1) said amine comprises an alkylamine or an alkanolamine.

5. A process according to claim 3, wherein step (2) is carried out at a temperature of 70°–90° C.

6. A process according to claim 3, wherein in step (4) the calcination is carried out in air at temperatures comprised within the range of from 500° to 700° C.

7. A process according to claim 3, wherein said phosphonoalkylsulfonic acids or phosphonoarylsulfonic acids of step (5) are selected from the group consisting of 2-phosphono-ethane-sulfonic acid, metaphosphono-benzenesulfonic acid and phosphonobenzene-3,5-disulfonic acid, and the reaction is carried out in an inert diluent at a temperature comprised within the range of from room temperature (20°–25° C.) up to about 100° C., with a concentration of the phosphono-alkyl-sulfonic acid or phosphono-aryl-sulfonic acid comprised within the range of from 0.1 molar up to the saturation value.

8. A process according to claim 3, wherein the gel obtained in step (3) is submitted to regeneration in order to yield back the hydrogen form of the zirconium phosphate before being submitted to the treatments of drying and calcination in step (4).

9. A process according to claim 3, wherein the gel is submitted to a treatment of shaping by an extrusion process.

10. A process according to claim 3, wherein the mixture obtained in step (3) is submitted to spray-drying and the so obtained dried solid is directly sent to step (5) for calcination.

11. A process for preparing the catalyst according to claim 2, comprising
(1) delaminating lamellar crystalline zirconium phosphate by means of the intercalation of an amine in an aqueous medium to obtain a colloidal dispersion of delaminated zirconium phosphate;
(2) mixing the dispersion prepared in step (1) with colloidal silica;
(3) gelling the resulting mixture by heating;
(4) drying and calcining the gel prepared in step (3); and
(5) reacting the calcined solid with a phosphono-alkyl-sulfonic acid or a phosphono-aryl-sulfonic acid.

12. A process as defined in claim 4, wherein in step (1) said amine used for the intercalation comprises an n-alkyl-amine.

13. A process as defined in claim 5 wherein said step (3) is carried out in the presence of an acidic gelling agent.

14. A process as defined in claim 13 wherein said gelling agent comprises acetic acid.

15. A process as defined in claim 6 wherein said calcination temperature is from 600° to 650° C.

16. A process as defined in claim 11 wherein step (3) is carried out in the presence of an acidic gelling agent.

* * * * *